(12) United States Patent  
Nakada et al.

(10) Patent No.: US 6,440,119 B1
(45) Date of Patent: Aug. 27, 2002

(54) INDWELLING CATHETER ASSEMBLY

(75) Inventors: Tsuneo Nakada; Masahiko Kobayashi, both of Yamanashi (JP)

(73) Assignee: Terumo Kabushiki Kaisha, Tokyo (JP)

( * ) Notice: Subject to any disclaimer, the term of this patent is extended or adjusted under 35 U.S.C. 154(b) by 87 days.

(21) Appl. No.: 09/617,032

(22) Filed: Jul. 14, 2000

Related U.S. Application Data

(62) Division of application No. 09/116,930, filed on Jul. 17, 1998.

(30) Foreign Application Priority Data

Jul. 22, 1997 (JP) .............................. 9-211346

(51) Int. Cl.[7] .............................................. A61M 31/00
(52) U.S. Cl. ...................................... 604/506; 604/500
(58) Field of Search .................... 604/21, 194, 169.01, 604/164.04, 103.08, 500, 506; 72/370.21

(56) References Cited

U.S. PATENT DOCUMENTS

| | | | |
|---|---|---|---|
| 2,744,429 A | | 5/1956 | Seely |
| 4,377,165 A | | 3/1983 | Luther et al. |
| 4,565,544 A | * | 1/1986 | Muller et al. ......... 604/164.04 |
| 4,579,554 A | * | 4/1986 | Glassman ............ 604/103.08 |
| 5,279,572 A | | 1/1994 | Hokama |
| 5,474,534 A | * | 12/1995 | Schlitt .................. 604/500 |
| 5,649,911 A | * | 7/1997 | Trerotola .............. 604/164.01 |
| 5,685,862 A | * | 11/1997 | Mahurkar ............... 604/194 |
| 5,827,216 A | * | 10/1998 | Igo et al. ................ 604/21 |
| 5,997,524 A | * | 12/1999 | Burbank et al. .......... 604/506 |
| 6,131,433 A | * | 10/2000 | Nakada et al. .......... 72/370.21 |

FOREIGN PATENT DOCUMENTS

| | | | |
|---|---|---|---|
| DE | 464931 | | 9/1928 |
| JP | 57-22836 | | 2/1982 |
| JP | 62-72649 | | 5/1987 |
| JP | 3-85046 | | 8/1991 |
| JP | 407024071 | * | 1/1995 |
| JP | 7-32803 | | 3/1998 |
| WO | 93/13821 | | 7/1993 |

* cited by examiner

*Primary Examiner*—Teresa Walberg
*Assistant Examiner*—Tsuneo Nakada
(74) *Attorney, Agent, or Firm*—Burns, Doane, Swecker & Mathis, LLP

(57) ABSTRACT

An indwelling catheter assembly includes a hollow outer catheter and an inner needle fitted inside the outer catheter. The inner needle has a groove in its outer circumference that is formed by press-working the inner needle. The press-formed groove extends axially along the inner needle from the leading end of the inner needle towards an opposite end of the inner needle.

14 Claims, 7 Drawing Sheets

INDWELLING CATHETER ASSEMBLY

This is a division of Ser. No. 09/116,930 filed Jul. 17, 1998.

FIELD OF THE INVENTION

The present invention generally relates to an indwelling catheter assembly to be needled to indwell in a blood vessel at an infusion time, for example.

BACKGROUND OF THE INVENTION

To effect infusion into a patient, an indwelling catheter connected with an infusion line is inserted into the blood vessel of the patient. This indwelling catheter is constructed of a hollow outer catheter and a hollow inner needle having a sloped edge face at its leading end that protrudes beyond the leading end of the outer catheter. The needle point of the inner needle is provided with an opening. The catheter is inserted into the blood vessel of the patient by first introducing the leading end of the needle into the blood vessel of the patient.

When the inner needle reaches the inside of the blood vessel, the blood enters the opening at the needle point and flows or flashes back into a transparent housing which is mounted at the root portion of the inner needle. This makes it possible to confirm that the inner needle has reached the blood vessel. At this time, the inner needle and the outer catheter are moved forward a slight distance to insert the leading end of the outer catheter into the blood vessel.

In known indwelling catheter assemblies, the inner circumference of the leading end of the outer catheter is closely fitted to the outer circumference of the inner needle so that the blood will not flow between the outer catheter and the inner needle. This makes it impossible to visually confirm by flashback of the blood whether or not the outer catheter has captured or been inserted into the blood vessel.

Thus, after confirming capture of the blood vessel by the inner needle, the inner needle and the outer catheter are delicately advanced by the operator based on the senses and experience of the operator. Because of this, the proper insertion of the outer catheter into the blood vessel is not always achieved, but may be too shallow or deep. This is partly because the spacing between the edge face of the inner needle and the leading end of the outer catheter is slightly different depending upon the kind and size of the indwelling catheter assembly, and the manufacturer of the indwelling catheter assembly. This is also due in part to the fact that the size of blood vessels in a patient(s) varies.

One proposal that attempts to address this problem is described in U.S. Pat. No. 5,279,572. This patent discloses an indwelling intravenous needle that includes a metallic internal needle, an external needle positioned over the internal needle so that the leading end of the external needle is set back from the leading end of the internal needle, and a plastic housing fitted to the rear end of the exterior needle. The patent describes providing a longitudinal groove on the surface of the inner needle. This groove extends from the leading edge face of the inner needle and terminates at a point within the housing. During use of the indwelling intravenous needle, the leading end of the internal needle is inserted into the vein cavity and the visual observation of blood flashback within the internal needle confirms that the internal needle has captured the vein cavity. Further advancement of the indwelling intravenous needle eventually causes the leading end of the external needle to capture the vein cavity and this capture can be observed as a result of blood flashback within the groove in the surface of the internal needle. The groove allows blood to flow between the inner surface of the exterior needle and the exterior surface of the internal needle.

The indwelling intravenous needle disclosed in the aforementioned patent is, however, susceptible of certain disadvantages and drawbacks. In one respect, the patent describes forming the groove on the surface of the internal needle by machining. The nature of this machining process causes a significant reduction in the wall thickness of the internal needle, thus resulting in a severe weakening of the needle wall. This weakened wall can cause problems during use of the needle, particularly given the rather thin nature of the needle. Further, the machining process results in a groove having relatively sharp or rough corners where the sides of the groove meet the outer surface of the needle. These roughened corners can cause damage to the external needle. Also, because the front portion of the internal needle is exposed beyond the leading end of the external needle, these sharp corners of the groove present the potential for scraping against and possibly causing damage to the vein during insertion of the indwelling intravenous needle into the vein. It is possible to attempt to round these sharp edges through use of a secondary working operation such as a polishing or deburring operation, but this undesirably complicates the manufacturing process and increases the manufacturing time.

In light of the foregoing, a need exists for an indwelling catheter assembly which permits visual confirmation that the indwelling catheter has captured a blood vessel, but which does not present the possibility of damaging the surrounding portion of the assembly or needlessly injuring the vein.

SUMMARY OF THE INVENTION

In accordance with one aspect of the present invention, an indwelling catheter assembly includes a hollow outer catheter, and an inner needle fitted inside the outer catheter. The inner needle has a sloped edge face at its leading end and is provided with a groove in its outer circumference that is formed by press-working the inner needle. The groove extends axially along the inner needle from the leading end of the inner needle towards an opposite end of the inner needle.

According to another aspect of the present invention, an indwelling catheter assembly includes a hollow outer catheter and an inner needle fitted inside the outer catheter. The inner needle has a sloped edge face at its leading end and is provided with a groove in its outer circumference that extends axially along the inner needle from the leading end of the inner needle towards the opposite end of the inner needle. The inner needle as viewed in a cross-section passing through the groove has a wall thickness that is the same throughout its entire circumferential extent.

Another aspect of the present invention involves a method of providing a groove in an inner needle that is to be used in an indwelling catheter assembly. The method involves positioning the inner needle in a press-forming machine, with the inner needle possessing a sloped edge face at its leading end. A longitudinally extending groove is then press formed in the outer circumference of the inner needle so that the groove extends along the inner needle from the leading end of the inner needle towards the opposite end of the inner needle.

BRIEF DESCRIPTION OF THE DRAWING FIGURES

The foregoing and additional features of the present invention will become more apparent from the following detailed description considered with reference to the accompanying drawing figures in which like elements are designated by like reference numerals and wherein.

DETAILED DESCRIPTION OF TM INVENTION

In the detailed description set forth below, the righthand side of the illustrations in FIGS. 1, 3, 4 and 6 will be referred to as the "root end" whereas the lefthand side of the illustrations will be referred to as the "leading end".

Figure 1:
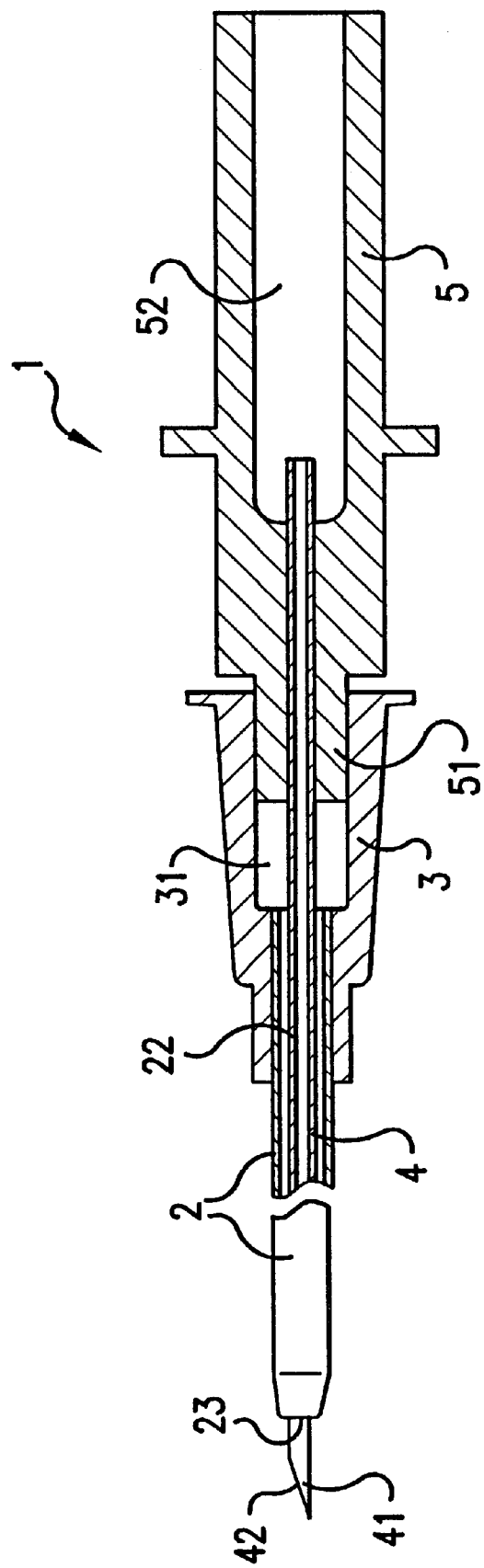
FIG. 1 is a longitudinal sectional view of the indwelling catheter assembly according to the present invention.

With reference initially to FIG. 1, the indwelling catheter assembly 1 of the present invention includes an outer catheter 2 and an inner needle 4. A hub 3 is fixed in a liquid-tight manner on the root end of the outer catheter 2. The root end of the hub 3 is provided with a cavity 31 that opens rearwardly. The hub 3 is made of a transparent or semi-transparent resin to permit the interior of the cavity 31 of the hub to be viewed from the outside.

Figure 2:
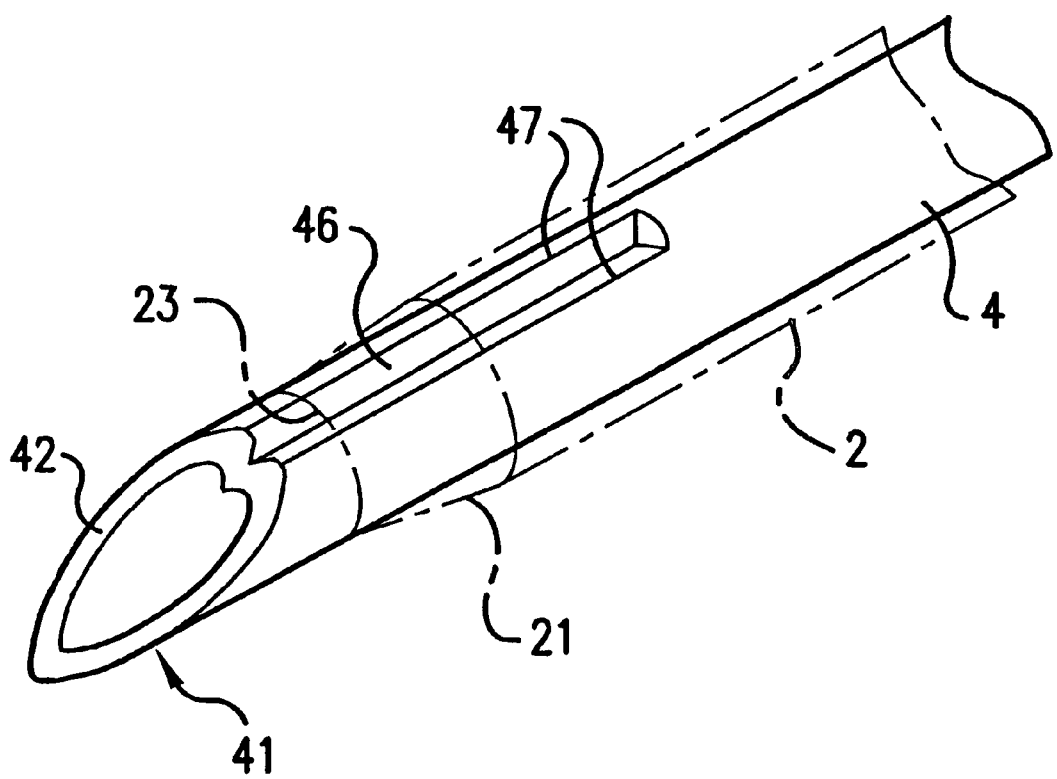
FIG. 2 is a perspective view of the leading end portion of the inner needle forming a part of the indwelling catheter assembly according to the present invention.

As seen with reference to FIG. 2, the internal diameter of the leading end of the outer catheter 2 is constricted or reduced in a generally tapering manner to form a constricted portion 21. The internal diameter of this constricted portion 21 is substantially equal to or slightly smaller than the external diameter of the inner needle 4 so that the inner circumferential surface of the constricted portion 21 closely contacts the outer circumferential surface of the inner needle 4 when the inner needle 4 is inserted into the outer catheter 2 in the assembled state. In this assembled state, the needle point 41 of the inner needle 4 protrudes or extends beyond the open leading end 23 of the outer catheter 2.

The portion of the outer catheter 2 located closer to the root end side than the constricted portion 21 has a larger internal diameter than the external diameter of the inner needle 4 so that in the assembled state a predetermined clearance 22 exists between the inner circumferential surface of the constricted portion 21 and the outer circumferential surface of the inner needle 4. This clearance 22 provides a passage for blood.

As seen in FIGS. 1 and 2, the leading end of the outer catheter 2 is tapered so that its external diameter gradually decreases toward the leading end. This tapering leading end of the outer catheter 2 facilitates the insertion of the assembly in a way that is designed to be minimally invasive.

The material from which the outer catheter 2 is fabricated is not necessarily limited to specific materials, but can preferably be exemplified by a variety of soft resins such as ethylene tetrafluoroethylene (ETFE), polyurethane or polyether nylon resin.

It is preferred that the outer catheter 2 possess semi-transparent or transparent characteristics which allow the interior of the outer catheter 2 to be visible along a portion of its length or the entirety of its length. Also, it is possible to blend an X-ray contrast medium into the material forming the outer catheter 2 to provide the outer catheter with a contrast function or radiopaque properties. Examples of a suitable X-ray contrast medium include barium sulfate or barium carbonate.

The inner needle 4 is hollow throughout its length and is made of a metallic material such as titanium, stainless steel, aluminum or an aluminum alloy, titanium or a titanium alloy. The leading end of the inner needle 4 is open and possesses a sharp needle point 41. This sharp needle point 41 has an edge face 42 that is sloped at a predetermined angle with respect to the axis of the inner needle 4. The inner needle 4 is designed to have a length which, as noted above, allows at least the needle point 41 of the inner needle 4 to protrude from or extend beyond the opening in the leading end 23 of the outer catheter 2.

Figure 5:
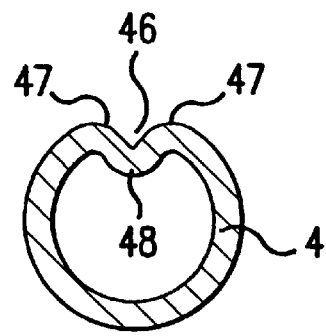
FIG. 5 is a cross-sectional view of the inner needle taken along the section line V—V in FIG. 3.
Figure 6:
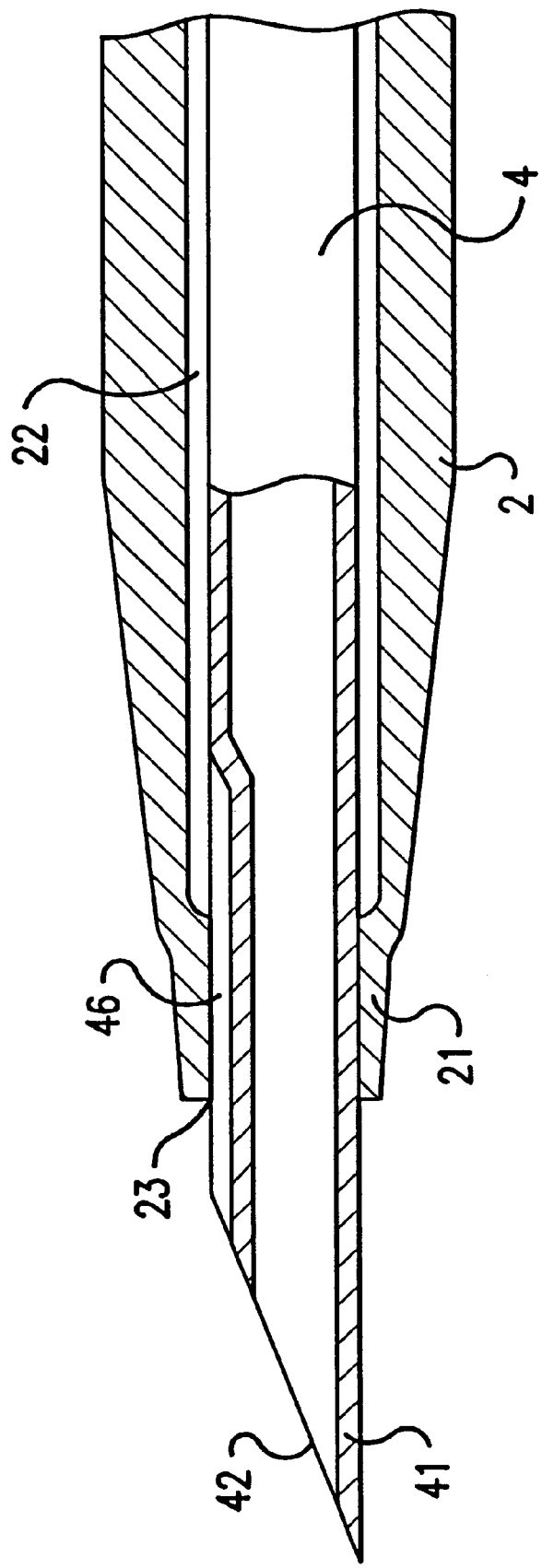
FIG. 6 is a longitudinal cross-sectional view of the front portion of the indwelling catheter assembly according to the present invention.
Figure 7:
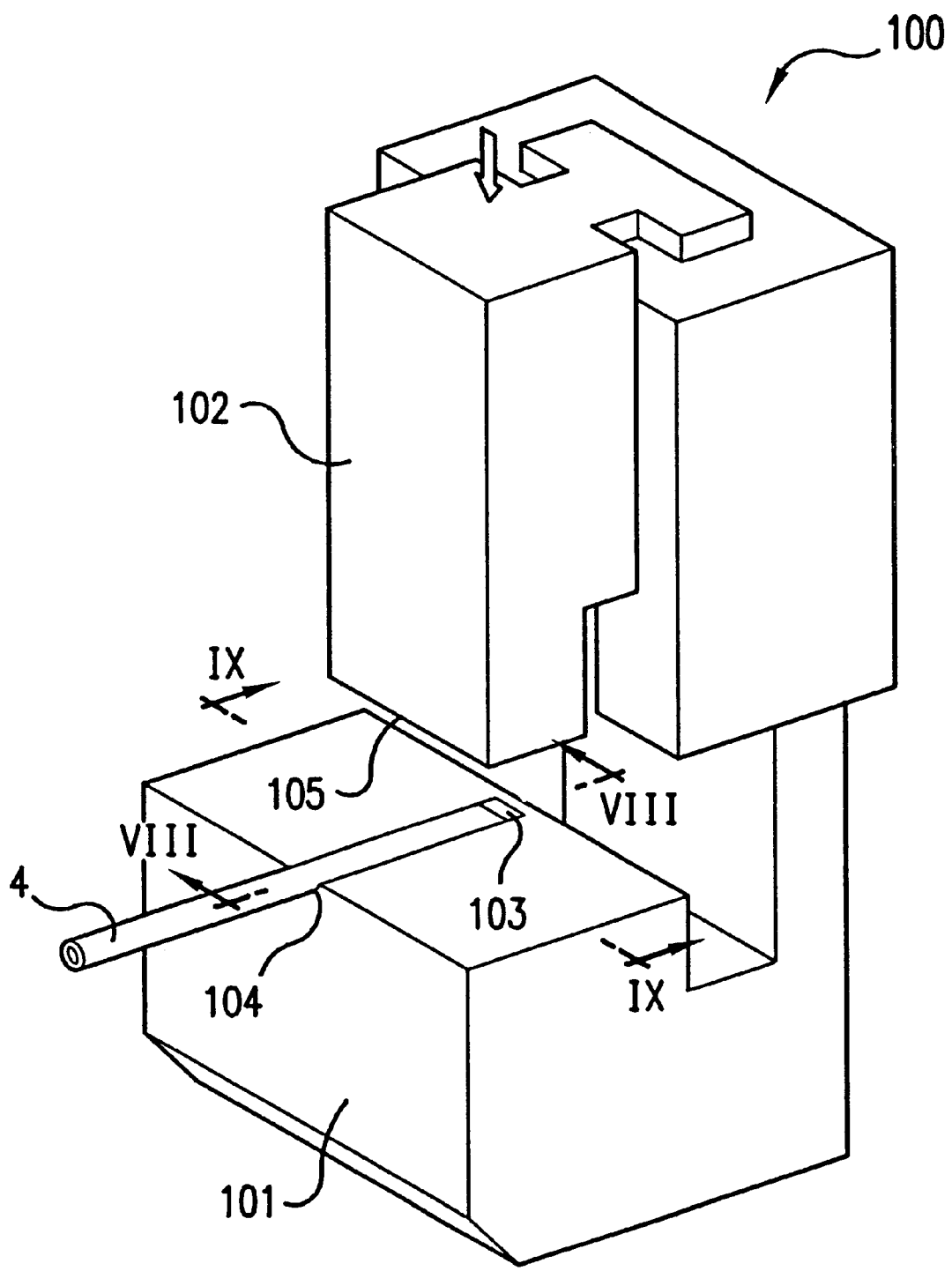
FIG. 7 is a perspective view of the machine used to press form the groove in the inner needle of the indwelling catheter assembly according to the present invention.

As seen with reference to FIGS. 2–6, a groove is formed in the outer circumference of the leading end of the inner needle 4. This groove 46 extends along the longitudinal direction of the inner needle 4. In the assembled state shown in FIG. 6, the groove 46 formed in the inner needle 4 is positioned to confront the constricted portion 21 of the outer catheter 2 and to include the axial region of the constricted portion 21. The axial extent of the groove 46 is greater than the axial extent of the constricted portion 21 of the outer catheter. Thus, as seen in FIG. 6, the groove is open at its leading end by virtue of the fact that it extends up to the leading end of the inner needle 4 (i.e., up to the needle point 41). The groove 46 extends from the sloping edge face of the inner needle 4 towards the root end of the inner needle 4 beyond the constricted portion 21 of the outer catheter 2.

The groove 46 is particularly configured so that the two longitudinally extending edges 47 of the groove 46, i.e. the boundary regions between the side walls of the groove 46 and the outer circumferential surface of the inner needle 4, are rounded. Thus, the edges 47 are not sharp and roughened and so there is little likelihood that the edges 47 of the groove 46 will damage the inner surface of the outer catheter 2 when the inner needle 4 is inserted into the outer catheter 2.

In addition, it is to be noted that the wall thickness of the inner catheter 4 in the region of the groove is the same as in the other areas of the inner needle 4. That is, the wall thickness of the inner needle is constant through its entire circumferential extent, including in the area of the groove 46. As seen in FIG. 5, the wall thickness of the inner needle 4 in a plane perpendicular to the longitudinal extent of the inner needle 4 and passing through the groove 46 is the same throughout. Thus, the portion of the inner needle 4 at which the groove 46 is located is not weakened and is thus not susceptible of the problems typically associated with a thinned and weakened needle wall.

As described in more detail below, the groove 46 in the inner needle 4 possesses the desirable characteristics discussed above by virtue of being formed through a press forming operation that is performed on the inner needle 4. When the inner needle 4 is elastically deformed by the press-working operation to form the groove 46, it is rather easy to produce the groove 46 in a way that results in rounded and smooth edges 47, thus not requiring secondary working operations. Moreover, the press forming operation does not thin the wall of the inner needle and so the inner needle 4 possesses a constant wall thickness throughout its circumferential extent. Further, by using a mold adapted to press-form several pieces at the same time, respective grooves 46 can be formed in each of a plurality of inner needles 4 in a single operation, thereby increasing the productivity.

Figure 3:
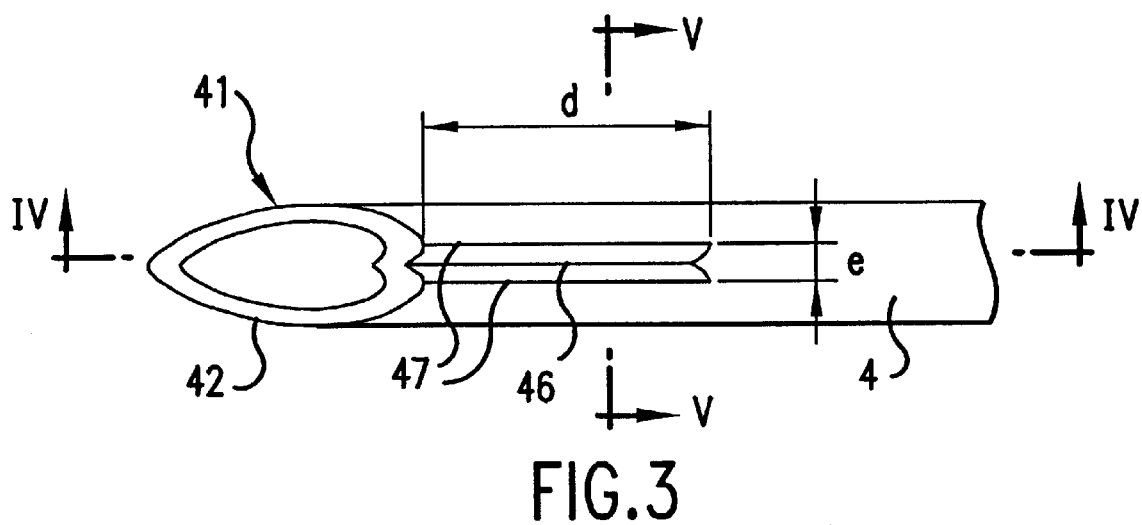
FIG. 3 is a top plan view of the leading end portion of the inner needle forming a part of the indwelling catheter assembly according to the present invention.
Figure 4:
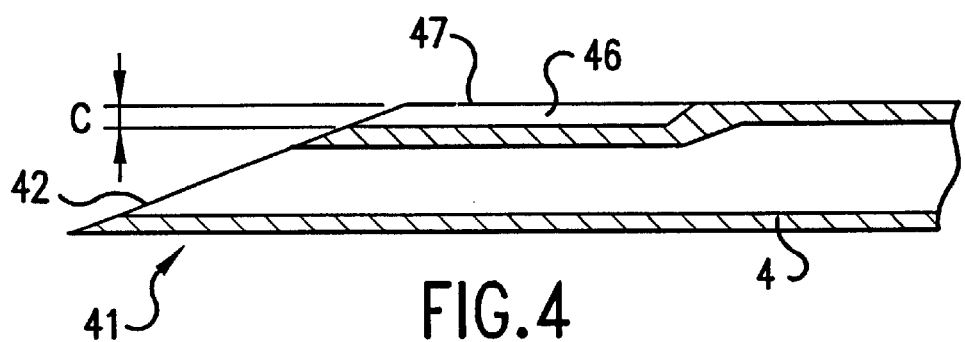
FIG. 4 is a longitudinal cross-sectional view of the leading end portion of the inner needle taken along the section line IV—IV in FIG. 3.

As shown in FIG. 3 and noted above, the groove 46 is formed to have a length d along the axial direction of the inner needle 4. The length d of the groove extends from the vicinity of the edge face 42 at the leading end of the inner tube 4.

The shape and size of the groove 46 is not particularly limited if the groove 46 can cover the contacting portions between the inner needle 4 and the outer catheter 2. In the illustrated construction, however, the groove 46 preferably has a maximum depth c of about 0.01 mm to 0.3 mm, more preferably about 0.03 mm to 0.15 mm. The groove 46 preferably has a length d of about 5 mm to 30 mm, more preferably about 5 mm to 15 mm. Moreover, the groove 46 preferably has a width e of about 0.1 mm to 1.0 mm, more preferably about 0.2 mm to 0.5 mm. The inner needle 4 can have a wall thickness throughout that is on the order of 0.09 mm to 0.23 mm.

In addition, the cross-sectional shape of the groove 46, and the maximum depth and width of the groove 46 can be constant or can vary along the length or longitudinal direction of the inner needle 4. For example, the groove 46 can be configured so that along a portion of the length of the groove 46, especially at the root end, the depth and/or width can be gradually decreased toward the base end. Also, it can be appreciated that through the provision of the press-working operation, a groove or grooves 46 having a complicated shape can be rather easily manufactured.

Turning back to FIG. 1, a hub or housing 5 is fixed in a liquid-tight manner on the root end of the inner needle 4. The root end of the hub 5 is provided with a cavity 52 that opens rearwardly. The housing 5 is preferably made of a transparent or semitransparent resin so that the interior of the cavity 52 in the hub is visible from outside.

A constricted joint 51 is formed at the leading end of the housing 5. This constricted joint 51 possesses a smaller outside diameter than the remainder of the housing 5 and is positioned in the cavity 31 at the root end of the hub 3 in the assembled state. In the assembled state, the leading end of the hub 5 is spaced from the end wall of the cavity 31 in the hub 3 as seen in FIG. 1. It can also be seen that the inner needle 4 extends throughout the axial extent of the outer cateter 2, throughout the axial extent of the hub 3 and into the housing 5, with the root end of the inner needle 4 terminating in the cavity 52 of the housing 5.

Examples of materials from which the two hubs 3, 5 can be individually manufactured include polyolefins such as polyethylene, polypropylene or a copolymer of ethylene and vinyl acetate, polyvinyl chloride, polymethyl methacrylate, polycarbonate, polybutadiene, polyamide or polyester.

An example of a manner of using the indwelling catheter assembly 1 according to the present invention is as follows.

Initially, with the indwelling catheter assembly 1 assembled in the manner shown in FIG. 1, the needle point 41 of the needle 4 is pierced through the skin of a patient. When the needle point 41 of the inner needle 4 is inserted into the blood vessel of the patient, the blood is fed back in the inner needle 4 towards the root end by the internal pressure (or blood pressure) of the blood vessel. As the blood is introduced into the interior of the housing or hub 5, the blood or flashback is visible through the hub 5. Upon viewing the blood in the hub, the user knows that the needle point 41 of the inner needle 4 has captured the blood vessel.

As the inner needle 4 and the outer catheter 2 are moved forward a small distance, the leading end of the outer catheter 2 is inserted into the blood vessel. As a result, blood flows from the leading end opening 23 of the inner needle 4 through the groove or clearance 46 in the inner needle, and further through the clearance 22 between the inner circumferential surface of the constricted portion 21 of the inner needle 4 and the outer circumferential surface of the inner needle 4. This blood flashback flows into the cavity 31 in the hub 3 and can be visually confirmed through the visible nature of the outer catheter 2 and hub 3. As a result, it is known that the leading end of the outer catheter 2 has captured the blood vessel.

After this, only the outer catheter 2 is further driven through the blood vessel into a predetermined indwelling position. The inner needle 4 is extracted from the outer catheter 2 by holding the outer catheter 2 with one hand and pulling the hub 5 toward the root end while gripping the hub 5 with the other hand.

The infusion is fed by connecting the infusion line with the hub 3 through a connector and by fixing the outer catheter 2 and the hub 3 with adhesive tape or the like. As a result, the infusion is injected into the blood vessel of the patient through the outer catheter 2.

As mentioned above, the groove 46 in the inner needle 4 is advantageously formed by a press-working or press-forming operation. This operation can be performed through use of an apparatus or machine 100 such as shown in FIGS. 7–10. The apparatus 100 includes a female mold 101 and a male mold 102. The male mold 102 is vertically movable with respect to the female mold 101.

The female mold 101 is provided with a generally U-shaped groove 104 for receiving the inner needle 4. The groove 104 possesses a diameter or radius of curvature that is substantially equal to or slightly larger than the external diameter or radius of curvature of the inner needle 4 to prevent the inner needle 4 from being crushed when pressed.

The inner needle 4 having the sloping edge face 42 formed in advance is positioned in the U-shaped groove 104 of the female mold 101. Because the groove that is to be formed in the inner needle 4 has to be formed along the axial direction of the inner needle beginning at the edge face of the inner needle in the manner shown in FIG. 2 for example, the location of the groove must be accurately adjusted to the position at which the groove is to be pressed on the inner needle 4.

Figure 8:
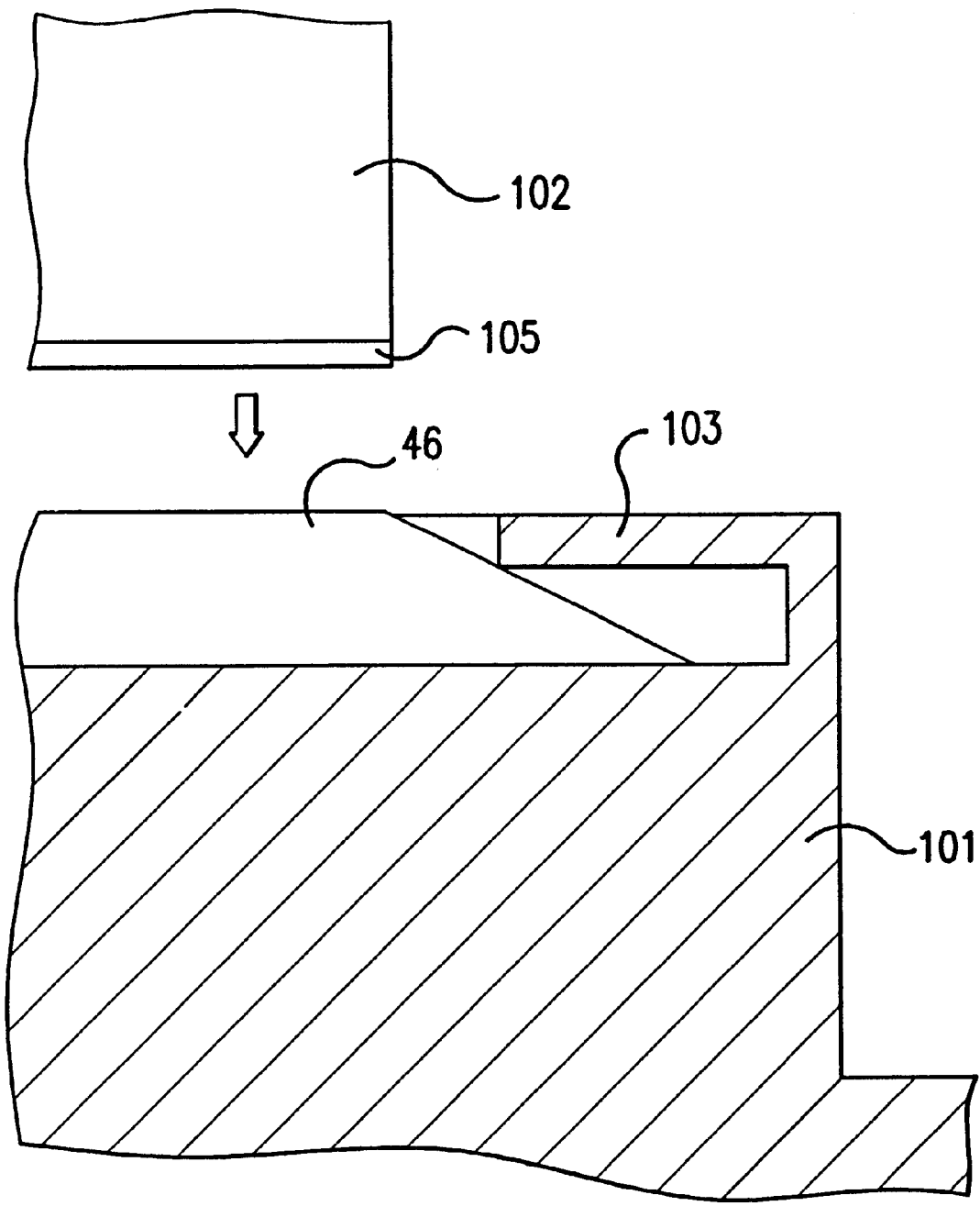
FIG. 8 is an enlarged cross-sectional view of the machine shown in FIG. 7 taken along the section line VIII—VIII in FIG. 7.
Figure 9:
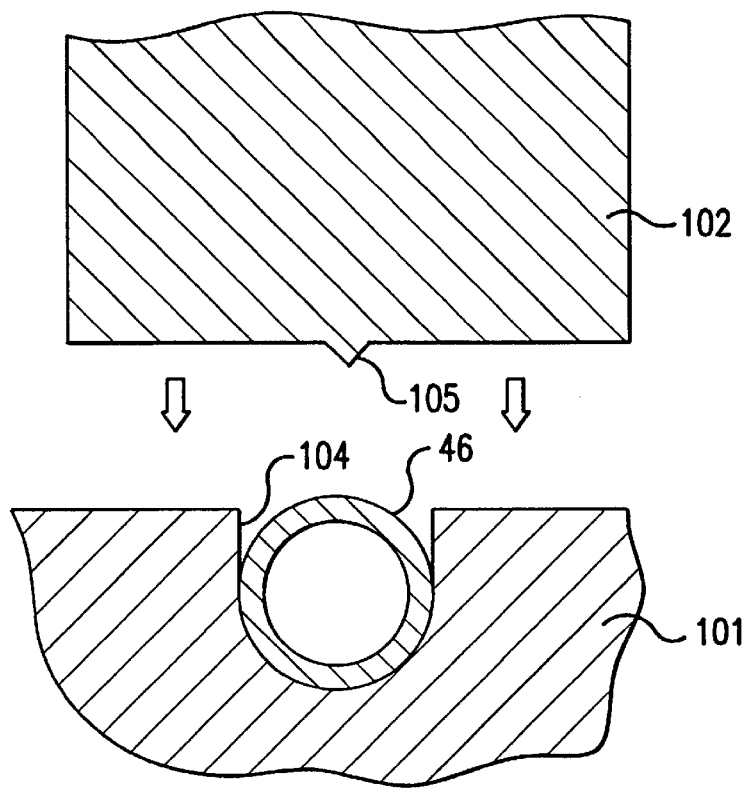
FIG. 9 is an enlarged cross-sectional view of the machine shown in FIG. 7 taken along the section line IX—IX in FIG. 7.
Figure 10:
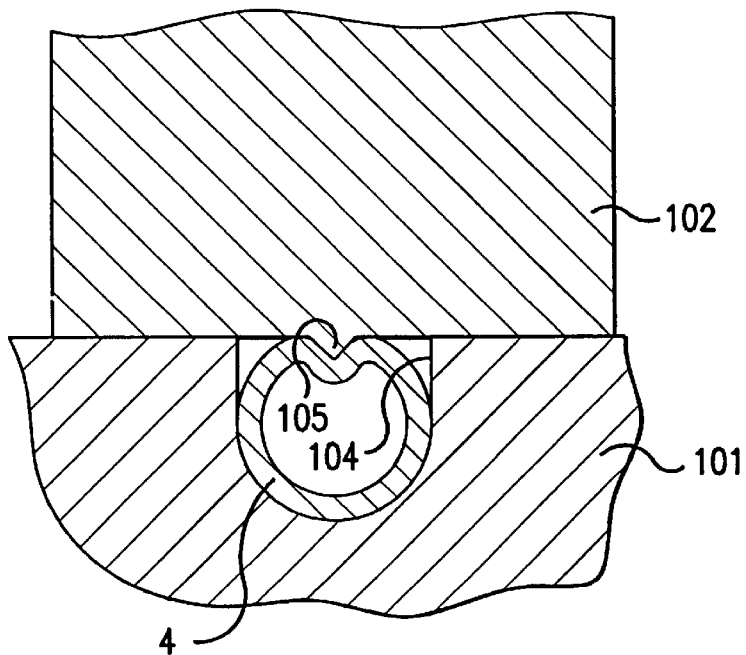
FIG. 10 is an enlarged cross-sectional view of a portion of the machine shown in FIG. 7 illustrating the press forming operation.

This positioning is achieved as best seen in FIG. 8 which is an enlarged illustration of the needle point portion of the inner needle 4 positioned in the groove 104 in the female mold 101. As shown, the sloping edge face of the inner needle 4 is positioned to abut against an overhang portion 103 positioned in overlying relation to the groove 104. With this arrangement, the edge face of the inner needle 4 can always be positioned and oriented in a predetermined rotational direction.

Although not shown, the position of the portion of the inner needle to be pressed can be adjusted by checking the inner needle to confirm the orientation of the edge face of the inner needle with two cameras.

After proper adjustment and positioning of the edge face of the inner needle 4, male mold 102 is moved vertically downward towards the female mold 101. The inner needle 4 is then pressed by a pressing projection 105 that extends outwardly from the end face of the male mold 102. The pressing projection possesses an axial extent equal to the axial or longitudinal extent of the groove 46 to be formed in the inner needle 4.

The working conditions for pressing the groove 46 in the inner needle 4 are not particularly limited, but may be suitably determined according to the material, the internal diameter and thickness of the inner needle 4. Under ordinary conditions, however, the pressing pressure is preferably on the order of 50 Kg/cm$^2$ to 300 Kg/cm$^2$, most preferably about 100 Kg/cm$^2$ to about 300 Kg/cm$^2$.

By virtue of the present invention, an indwelling catheter assembly is provided that permits visual confirmation of when the outer catheter has captured the blood vessel through flashback of blood into the outer catheter. As a result, the insertion of the indwelling catheter into a blood vessel can be performed easily and accurately.

According to the indwelling catheter assembly of the present invention the groove that allows the blood flashback is formed by a press-working operation applied to the outer circumference of the inner needle. The indwelling catheter assembly of the present invention can be easily manufactured and worked, and can have a high working accuracy. Further, this is achieved without adversely affecting the strength of the inner needle wall because the groove in the inner needle that allows flashback of blood into the outer catheter is press-formed. Further, the groove does not possess sharp edges that might damage the outer catheter.

The principles, preferred embodiments and modes of operation of the present invention have been described in the foregoing specification. However, the invention which is intended to be protected is not to be construed as limited to the particular embodiments described. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the invention be embraced thereby.

What is claimed is:

1. An indwelling catheter assembly comprising:
    a hollow outer catheter; and
    an inner needle fitted inside said outer catheter, said inner needle possessing a leading end and an outer circumference, the inner needle having a sloped edge face at the leading end, said inner needle having a groove in its outer circumference that is formed by press-working said inner needle, said groove extending axially along said inner needle from the leading end of the inner needle towards an opposite end of the inner needle.

2. The indwelling catheter assembly as set forth in claim 1, wherein said groove includes side walls, the side walls intersecting the outer circumference of the inner needle at rounded edges.

3. The indwelling catheter assembly as set forth in claim 1, wherein said inner needle possesses a wall thickness that is the same throughout its circumferential extent as seen in a cross-sectional view passing through the groove.

4. The indwelling catheter assembly as set forth in claim 1, wherein the outer catheter has a leading end with a tapering outer circumference, the leading end of the outer catheter tightly surrounding the inner needle, said groove extending axially beyond the leading end of the outer catheter.

5. The indwelling catheter assembly as set forth in claim 1, including a hub mounted in a liquid-tight manner on a root end of the outer catheter, the hub being at least semi-transparent.

6. The indwelling catheter assembly as set forth in claim 5, including a housing that is connected to a root end of the hub, said housing being at least semi-transparent.

7. The indwelling catheter assembly as set forth in claim 6, wherein the root end of the hub includes a cavity having an end wall, said housing having a leading end of reduced outer diameter that is fitted within the cavity in the hub so that the leading end of the housing is spaced from the end wall of the cavity.

8. The indwelling catheter assembly as set forth in claim 6, wherein said inner needle extends through said hub and into said housing.

9. An indwelling catheter assembly comprising:
    a hollow outer catheter; and
    an inner needle fitted inside said outer catheter, said inner needle possessing a leading end and an outer circumference, the inner needle having a sloped edge face at the leading end, said inner needle having a groove in its outer circumference that extends axially along said inner needle from the leading end of the inner needle towards an opposite end of the inner needle, said inner needle as viewed in a cross-section passing through said groove having a wall thickness that is the same throughout its entire circumference.

10. The indwelling catheter assembly as set forth in claim 9, wherein said groove includes side walls, the side walls intersecting the outer circumference of the inner needle at edges that are rounded.

11. The indwelling catheter assembly as set forth in claim 9, including a hub mounted in a liquid-tight manner on a root end of the outer catheter, the hub being at least semi-transparent.

12. The indwelling catheter assembly as set forth in claim 11, including a housing that is connected to a root end of the hub, said housing being at least semi-transparent.

13. The indwelling catheter assembly as set forth in claim 12, wherein the root end of the hub includes a cavity having an end wall, said housing having a leading end of reduced outer diameter that is fitted within the cavity in the hub so that the leading end of the housing is spaced from the end wall of the cavity.

14. The indwelling catheter assembly as set forth in claim 12, wherein said inner needle extends through said hub and into said housing.

* * * * *